United States Patent [19]

Mehta et al.

[11] Patent Number: 4,950,432
[45] Date of Patent: Aug. 21, 1990

[54] POLYENE MICROLIDE PRE-LIPOSOMAL POWDERS

[75] Inventors: Reeta Mehta; Gabriel Lopez-Berestein, both of Houston, Tex.

[73] Assignee: Board of Regents, The University of Texas System, Austin, Tex.

[21] Appl. No.: 109,813

[22] Filed: Oct. 16, 1987

[51] Int. Cl.$^5$ .................. A61K 9/133; A61K 9/127; B01J 13/02

[52] U.S. Cl. ........................... 264/4.6; 514/31; 514/37; 424/450; 424/502

[58] Field of Search ................ 424/450, 490; 428/402.2, 402.21; 264/4.6, 4.1; 514/31, 37

[56] References Cited

U.S. PATENT DOCUMENTS

| | | | |
|---|---|---|---|
| 3,993,754 | 11/1976 | Rahman et al. | 424/450 X |
| 4,186,183 | 1/1980 | Steck et al. | 424/450 |
| 4,229,360 | 10/1980 | Schneider et al. | 264/4.6 |
| 4,235,871 | 11/1980 | Papahadjopoulos et al. | 424/450 |
| 4,241,046 | 12/1980 | Papahadjopoulos et al. | 424/450 X |
| 4,247,411 | 1/1981 | Vanlerberghe et al. | 264/4.6 |
| 4,308,166 | 12/1981 | Marchetti et al. | 424/450 |
| 4,311,712 | 1/1982 | Evans et al. | 514/773 |
| 4,370,349 | 1/1983 | Evans et al. | 514/785 |
| 4,411,894 | 10/1983 | Schrank et al. | 514/78 X |
| 4,427,649 | 1/1984 | Dingle et al. | 424/450 |
| 4,460,577 | 7/1984 | Moro et al. | 424/450 |
| 4,515,736 | 5/1985 | Deamer | 264/4.3 |
| 4,529,561 | 7/1985 | Hunt et al. | 264/4.3 |
| 4,610,868 | 9/1986 | Fountain et al. | 264/4.1 X |
| 4,622,188 | 11/1986 | Adamich et al. | 264/4.6 |
| 4,663,167 | 5/1987 | Lopez-Berestein et al. | 514/37 |
| 4,687,762 | 8/1987 | Fukushima et al. | 514/37 X |
| 4,731,210 | 3/1988 | Weder et al. | 264/4.3 |
| 4,737,323 | 4/1988 | Martin et al. | 424/450 X |
| 4,744,989 | 5/1988 | Payne et al. | 514/31 X |
| 4,762,720 | 8/1988 | Jizomoto | 264/4.3 X |
| 4,766,046 | 8/1988 | Abra et al. | 264/4.3 X |
| 4,812,312 | 3/1989 | Lopez-Berestein | 264/4.1 X |
| 4,830,858 | 5/1989 | Payne et al. | 424/450 |
| 4,863,739 | 9/1989 | Perez-Soler | 424/450 |

FOREIGN PATENT DOCUMENTS

| | | | |
|---|---|---|---|
| A0087993 | 9/1983 | European Pat. Off. | 264/4.1 |
| 2112426 | 6/1972 | France | 514/37 |
| A2390159 | 12/1978 | France | 264/4.1 |
| 2593394 | 7/1987 | France | 424/450 |
| 87/01933 | 4/1987 | PCT Int'l Appl. | 424/450 |
| 87/01938 | 4/1987 | PCT Int'l Appl. | 424/450 |
| 88/03831 | 4/1989 | PCT Int'l Appl. | 424/450 |
| WO86/01102 | 2/1986 | World Int. Prop. O. | 424/450 |

OTHER PUBLICATIONS

Szoka et al., Ann. Rev. Biophys. BioEng., (1980), 9:467-508.
Ganapathi et al., Biochemical Pharmacology, 33:698-700, (1984).
Olsen et al., Eur. J. Cancer Clin. Oncol., 18:167-176, (1982).
International Search Report, Mar. 16, 1989.
Lopez-Berestein et al., 'Treatment and Prophylaxis ... with Liposome-Encapsulated Amphotericin B', *J. Infect. Dis.*, vol. 147, No. 5, (1983), pp. 939-945.

*Primary Examiner*—Richard D. Lovering
*Assistant Examiner*—John M. Covert
*Attorney, Agent, or Firm*—Arnold, White & Durkee

[57] ABSTRACT

The present invention involves a process for producing fine powder suitable for the preparation of antifungal polyene microlide-containing liposomes upon suspension in an aqueous solution. This process comprises the following steps. Quantities of polyene macrolide and phospholipids are dissolved respectively in a first solvent and a second solvent to form a first solution and a second solution. The first solution and the second solution are mixed in a desired ratio to form a mixture. The first solvent and the second solvent are then removed from the mixture, for example by evaporation, to form a residue. The residue is then dissolved in a third solvent comprising tertiary butanol and methylene chloride to form a third solution. The third solvent is then removed from the third solution to form a remnant. The remnant is then dissolved in a solvent consisting essentially of tertiary butanol to form a fourth solution. The fourth solution is then filtered through a filter having orifices of between about 0.05 and 0.5 micrometers in diameter to produce a filtrate. The filtrate is lyophilized to remove the tertiary butanol and a fine powder remains. This fine powder may be used to form polyene macrolide-containing liposomes by simple incubation or suspension in an aqueous solution.

18 Claims, No Drawings

POLYENE MICROLIDE PRE-LIPOSOMAL POWDERS

BACKGROUND OF THE INVENTION

The present invention relates to a composition of matter usable to form liposomes comprising antifungal polyene macrolides and the production thereof.

Clinical observations and animal experimental studies have added to the understanding of host-fungal interactions. It is becoming recognized that host defense against fungal disease is multifactorial and may vary, depending on the etiologic agent. The mechanisms of resistance are not well defined in most instances, but various innate barriers and cell-mediated immune responses seem to be of primary importance. Clearly, debilitation of innate defenses and of cell-mediated immune responses can increase an individual's susceptibility to severe fungal disease from opportunistic agents such as *Cryptococcus neoformans* and species of *Candida* and *Aspergillus*, as well as from fungal pathogens such as *Histoplasma capsulatum* and *Coccidioides immitis*. The difficulty in gaining a complete understanding of the critical host defenses has been further complicated by many studies that show fungi may affect various host immune functions adversely. Although it is too early to evaluate the clinical importance of many of these experimental findings, investigators have demonstrated that fungi impair neutrophil function, induce IgE responses, and cause suppression of cell-mediated immune responses.

Host changes likely to be associated with increased susceptibility may be accidentally induced, as in traumatic injuries (such as burns or puncture wounds); self-induced, as in chronic alcoholism; naturally occurring, as in diabetes mellitus, various congenital immune deficiencies, collagen diseases, lyaphoreticular neoplastic disease, and other types of tumors; or iatrogenically induced by instrumentation (such as catheterization), surgical procedures (such as open heart surgery), or by use of cytotoxic drugs (as in an attempt to prevent graft rejection and to treat neoplastic disease), corticosteroid therapy, and long-term use of broad-spectrum antibiotics.

Chemical factors that aid resistance to fungal diseases are poorly defined. Knowledge of these substances is based primarily on circumstantial evidence at the clinical level and in vitro observations at the experimental level. Hormonally associated increases in lipid and fatty acid content on the skin occurring at puberty have been correlated with increased resistance to tinea capitis caused by the dermatophyte *Microsporum audouinii*, although pubescent changes are not the sole factors in resistance. Substances in serum, cerebrospinal fluid, and saliva may limit growth of *Cryptococcus neoformans*, and basic peptides in body fluids have been shown to inhibit *Candida albicans*.

Results of clinical and experimental studies indicate that *C. albicans, C. neoformans, Aspergillus fumigatus*, and *C. immitis* activate the alternative pathway of the complement cascade. Because of the polysaccharide nature of fungal cell walls, it is expected that all medically important fungi activate complement. Such activation may be important in defense against some mycoses; a positive correlation has been demonstrated between animals deficient in late-acting complement components (C3-C9) and increased susceptibility to fungi such as *C. neoformans* and *C. albicans*. Assuming that phagocytic cells are important in resistance to fungi, complement activation may play a role by provoking an acute inflammatory response on generation of complement fragments C3a and C5a, and by coating the fungal elements with opsonic fragments C3b and C3d for ingestion by phagocytic cells.

The systemic mycoses of humans and other animals are caused by some fungi that are pathogenic and cause disease in the healthy host, and by other fungi (opportunistic pathogens) that are usually innocuous but cause disease in patients whose immune defenses are impaired. Some of these fungi may be saprophytes in nature (soil, bird droppings), whereas others are a part of the normal human flora (commensals). In no case are humans the solitary or necessary host.

An example of a soil saprophyte is *Histoplasma capsulatum*, which commonly causes infection in endemic areas; 80%-90% of adults react positively to histoplasmin in delayed cutaneous hypersensitivity tests. An example of an opportunistic pathogen is *Candida albicans*, normally present in the oral cavity, gastrointestinal tract, and probably the skin. In the patient with acute leukemia, however, *C. albicans* is commonly present in blood, causing a fulminant, usually fatal, septicemia. Other opportunistic infections are seen in patients with diabetic acidosis (mucormycosis) and Hodgkin's disease (for example, cryptococcosis and histoplasmosis). The pathogenesis of these mechanisms is obscure, but cell-mediated immunity seems to be essential for a good prognosis.

Neither active vaccines nor passive immune serum immunization has been sufficiently successful to result in commercially available preparations.

Treatment of active disease may be symptomatic (for example, pain relief), sometimes surgical (resection of irremediably damaged tissue and correction of hydrocephalus), and, most successfully, chemotherapeutic (Table 1). Among the chemotherapeutic agents commonly used are hydroxystilbamidine isethionate, amphotericin B, 5-fluorocytosine (Flucytosine), miconazole, and ketoconazole. Response to these drugs varies according to the fungus, type of disease, and course of illness. For example, response is good in most *B. dermatitidis* infections, but is poor in most diseases caused by *A. fumigatus*. Response is better for skin lesions caused by *B. dermatitidis* than for meningitis due to *C. immitis;* response is better in chronic cryptococcosis than in fulminant candidiasis. Table 1 shows a listing of some systemic mycoses and generally accepted chemotherapeutic agents.

TABLE 1
CHEMOTHERAPEUTIC AGENTS FOR SYSTEMIC MYCOSES

| Disease | First Choice | Second Choice |
|---|---|---|
| Aspergillosis | Amphotericin B | Ketoconazole |
| Blastomycosis | Amphotericin B | Hydroxystilbamidine isethionate |
| Candidiasis | Amphotericin B | Flucytosine or ketoconazole |
| Coccidioidomycosis | Amphotericin B | Ketoconazole |
| Cryptococcosis | Amphotericin B Flucytosine | Either drug alone* |
| Histoplasmosis | Amphotericin B | Ketoconazole* |
| Mucormycosis | Amphotericin B | Miconazole* |
| Paracoccidioidomycosis | Amphotericin B | Sulfonamides, Ketoconazole* |

*Depending on minimal inhibitory concentration necessary for the fungus.

Infection is the cause of death in 51% of patients with lymphoma and 75% of patients with leukemia. Although bacteria are the causative organisms of many such infections, fungi account for 13% of the fatal infections in patients with lymphoma and for more than 20% of patients with leukemia. The fungus *Candida albicans* causes more than 80% of these infections, and *Aspergillus* spp. is also a frequent cause of such infections. In addition, fungal infection is a major cause of morbidity and mortality in patients with congenital and acquired deficiencies of the immune system. Much concerted effort has been expended in search of agents useful in treating fungal infections of humans. As a result, many compounds have been isolated and shown to have antifungal activity, but problems associated with solubility, stability, absorption, and toxicity have limited the therapeutic value of most of them in human infections. The most useful antifungal antibiotics fall into one of two categories: those that affect fungal cell membranes and those that are taken up by the cell and interrupt vital cellular processes such as RNA, DNA, or protein synthesis. Table 2 lists some useful antifungal agents and their mechanisms of action.

TABLE 2
SOME USEFUL ANTIFUNGAL AGENTS, THEIR CHEMICAL CLASSIFICATION, AND THEIR MECHANISMS OF ACTION

| Class | Compounds | Mechanism |
| --- | --- | --- |
| Polyene | Amphotericin B Nystatin | Interacts with sterols (ergosterol) in fungal cell membrane, rendering cells selectively permeable to the outflow of vital constituents, e.g. potassium |
| Imidazole | Miconazole Clotrimazole Ketoconazole | Inhibits demethylation of lanosterol thus preventing formation of ergosterol, a vital component of fungal cell membrane; also has a direct cidal effect on fungal cells |
| Pyrimidine | 5-Fluorocytosine | Is taken up and deaminated by susceptible cell to form 5-fluorouracil, which in turn inhibits RNA synthesis; also thought to inhibit thymidylate synthetase and DNA synthesis |
| Grisan | Griseofulvin | Binds to tubulin and inhibits microtubule assembly |
| 3-Arylpyrrole | Pyrrolnitrin | Appears to inhibit terminal electron transport between succinate or NADH and coenzyme Q |
| Glutaramide | Cycloheximide | Inhibits protein synthesis at 80S ribosomal level preventing transfer of aminoacyl tRNA to the ribosome |

The polyene macrolide antibiotics are secondary metabolites produced by various species of Streptomyces. Several common features of these compounds are useful in classifying the more than 80 different polyenes that have been isolated. All are characterized by a macrolide ring, composed of 26-38 carbon atoms and containing a series of unsaturated carbon atoms and hydroxyl groups. These features of the molecule contribute to the polyenes' amphipathic properties (those relating to molecules containing groups with different properties, for example, hydrophilic and hydrophobic). The ring structure is closed by the formation of an internal ester or lactone bond (FIG. 1). The number of conjugated double bonds vary with each polyene, and the compounds are generally classified according to the degree of unsaturation.

Toxic effects of polyene macrolides appear to be dependent on binding to cell membrane sterols. Thus, they bind to membranes of fungus cells as well as to those of other eukaryotic cells (human, plant, and protozoa), but not to bacterial cell membranes, which do not contain membrane sterols. The interaction of polyene macrolides with mammalian and fungal membrane sterols results in transmembrane channels that allow the leakage of intracellular components leading to cell deaths.

The usefulness of an antibiotic is usually measured by the differential sensitivity of the pathogen and host. Two polyene macrolides agents, nystatin and amphotericin B, are relatively specific for fungi and have thusfar proven to have therapeutic usefulness in humans. The relative specificity of these two polyene macrolides may be based on their greater avidity for ergosterol, the principal sterol of fungal membranes, compared to cholesterol, the principal sterol of human cell membranes.

Amphotericin B is a heptaene macrolide with seven resonating carbon bonds. The compound was first isolated from broth filtrates of *S. nodosum* in 1956. Like other polyene macrolide antibiotics, amphotericin B is insoluble in water. The problem of its solubility has been circumvented by combining the antibiotic with sodium deoxycholate and sodium phosphate and hydrating the mixture with sterile water or saline. Amphotericin B is the polyene antibiotic thusfar most sufficiently nontoxic to humans that it has been used parenterally at effective doses against various fungi.

Nystatin, first isolated from *S. noursei*, is structurally related to amphotericin B, but is not classified as a heptaene because the conjugated portion of the ring is interrupted and thus forms a tetraene and a diene. Tolerated well both orally and topically, the drug is not available for intravenous use because of its presumed high toxicity and aqueous insolubility. Nystatin is available as oral tablets (500,000 units) or as an ointment for topical use (100,000 units/g). It is used in the management of cutaneous and mucocutaneous candidiasis.

It has recently been shown that the encapsulation of certain drugs in liposomes before administration to the patient can markedly alter the pharmacokinetics, tissue distribution, metabolism and therapeutic efficacy of these compounds. Liposomes may be defined as lipid vesicles which are formed spontaneously on addition of an aqueous solution to a dry lipid film. Further, the distribution and pharmacokinetics of these drugs can be modified by altering the lipid composition, size, charge and membrane fluidity of the liposome in which they are encapsulated.

Recently, liposomes have been used as carriers of amphotericin B for treatment of murine leishmaniasis (New, R.R.C., et al., "Antileishmanial Activity of Amphotericin and Other Antifungal Agents Entrapped in Liposomes." *J. Antimicrob. Chemother.*, Vol. 8 (1981), pp. 371-381), histoplasmosis (Taylor, R.L., et al., "Amphotericin B in Liposomes: A Novel Therapy for histoplasmosis." *Am. Rev. Respir. Dis.*, Vol. 125 (1982), pp. 610-611), cryptococosis (Graybill, J.R., et al., "Treatment of Murine Cryptococosis with Liposome-Associated Amphotericin B." *J. Infect. Dis.*, Vol. 145

(1982), pp. 748–752). and candidiasis (Tremblay, C., et al., "Comparative Efficacy of Amphotericin B (AMB) and Liposomal AMB (lip-AMB) in Systemic Candidiasis in Mice." *Abstr.* 1983 *ICAAC,* No. 755 (1983), p. 222). Liposome-encapsulated Amphotericin B has also been used for treatment of coccidioidomycosis in the Japanese macaque (Graybill, J.R., et al., "Treatment of Coccidioidomydosis (cocci) in Primates Using Liposome Associated Amphotericin B (Lipo-AMB)." *Abstr.* 1982 *ICCAC,* No. 492 (1982), p. 152).

The treatment of fungal infections remains a major problem in spite of the availability of effective antifungal drugs such as the polyenes. Most of the available polyene antibiotics have toxic side effects that limit their clinical application. Nystatin, a tetraene-diene polyene macrolide antibiotic, has high hydrophobicity, which has precluded its effective systemic administration. It has been used as suspensions prepared in various ways and administered to the patients orally. However, these studies have generally failed to document a beneficial effect of nystatin administration against systemic fungal infections.

The present inventors have recently demonstrated that liposome-encapsulated amphotericin B may be used to treat experimental murine candidiasis (Lopez-Berestein et al., J. Infect. Dis., Vol. 150, pp 278–283 (1984) and in the treatment of fungal infections in patients with leukemia and lymphoma (Lopez-Berestein et al., J. Infect. Dis., Vol. 151, pp 704–71 (1985).

SUMMARY OF THE INVENTION

The present invention involves a process for producing fine powder suitable for the preparation of antifungal polyene microlide-containing liposomes upon suspension in an aqueous solution. This process comprises the following steps. Quantities of polyene macrolide and phospholipids are dissolved respectively in a first solvent and a second solvent to form a first solution and a second solution. The first solution and the second solution are mixed in a desired ratio to form a mixture. The first solvent and the second solvent are then removed from the mixture, for example by evaporation, to form a residue. The residue is then dissolved in a third solvent comprising tertiary butanol and methylene chloride to form a third solution. The third solvent is then extracted by evaporation from the third solution to form a remnant. The remnant is then dissolved in a solvent consisting essentially of tertiary butanol to form a fourth solution. The fourth solution is then filtered through a filter having orifices of between about 0.05 and 0.5 micrometers in diameter to produce a filtrate. The filtrate is lyophilized to remove the tertiary butanol and a fine powder remains. This fine powder may be used to form polyene macrolide-containing liposomes by simple incubation or suspension in an aqueous solution.

DETAILED DESCRIPTION OF THE PREFERRED EMBODIMENT

A stable powder suitable for the direct preparation of liposome-incorporated antifungal polyene macrolides may be made by a process of the present invention. While the conditions described herein are specifically applicable to nystatin and amphotericin B, other polyene macrolide antifungals may be likewise used, but with minor modifications of procedure apparent to those skilled in the art upon a minimal amount of experimentation.

The process for pre-liposomal polyene macrolide powder formation of the present invention involves dissolution of an antifungal polyene macrolide such as nystatin or amphotericin B in a first organic solvent such as methanol to form a first solution. Phospholipids are dissolved in a second organic solvent such as, for example, chloroform, to form a second solution. The first solution and the second solution are mixed to form a first mixture having a ratio of antifungal polyene macrolide to phospholipid between about 1:5 and about 1:50, preferably of about 1:10. The organic solvents are removed from the mixture, for example, by solvent evaporation under reduced pressure and at a temperature between about 35° C. and about 45° C., until a residue such as a dry film is formed. The residue is then dissolved in a quantity of a third organic solvent such as a mixture of tertiary butanol and methylene chloride in a ratio between about 2:1 (preferred for nystatin) and about 1:40 (preferred for amphotericin B) and the solvent evaporated to leave a remnant. The remnant is dissolved in a solvent consisting essentially of tertiary butanol to form a fourth solution which is warmed, if necessary for clarification, and passed through a filter having orifices of between about 0.05 and 0.5 micrometers (um) in diameter. If warming is desired to clarify the fourth solution, particularly with amphoterecin B, the warming is preferably to a temperature between about 50° C. and about 70° C. The filtrate is subjected to freezing, for example, with dry ice-acetone. The frozen material is then lyophilized until essentially all solvent is removed. After lyophilization, a fine pre-liposomal polyene macrolide powder is produced. This powder is readily and stably stored under commonly available dry and cool storage conditions.

The above-described pre-liposomal polyene macrolide powder may be easily used to reconstitute a liposome suspension according to the following general procedure. The powder is added to an aqueous solution such as pyrogen-free saline, and allowed to incubate at 25° C. to 45° C. for 1–10 minutes for a liposome suspension to form. Polyene macrolide content may be measured by dissolution of the liposomes in methanol and monitoring of optical density at a wavelength characteristic for polyene macrolide absorption.

Representative, suitable phospholipids in the present invention are phosphatidylcholine, both naturally occurring and synthetically prepared, phosphatidic acid, phosphatidylserine, phosphatidylethanolamine, sphingolipids, phosphatidyglycerol, spingomyelin, cardiolipin, glycolipids, gangliosides, cerebrosides and the like used either singularly or intermixed such as in soybean phospholipids.

More particularly useful phospholipids include egg phosphatidylcholine, dilaurylphosphatidylcholine, dimyristoylphosphatidylcholine, dipalmitoylphosphatidylcholine, distearoylphosphatidylcholine, 1-myristoyl-2palmitoylphosphatidylcholine, 1-palmitoyl-2-myristoyl phosphatidylcholine, 1-stearoyl-2-palmitoyl phosphatidylcholine, dioleoylphosphatidylcholine, dilauryloylphosphatidylglycerol, dimyristoylphosphatidylglycerol, dipalmitoylphosphatidylglycerol, distearoylphosphatidylglycerol, dioleoylphosphatidylglycerol, dimyristoyl phosphatidic acid, dipalmitoyl phosphatidic, dimyristoyl phosphatidylethanolamine, dipalmitoyl phosphatidylethanolamine, dimyristoyl phosphatidylserine, dipalmitoyl phosphatidylserine, brain phosphatidylserine, brain sphingomyelin, dipalmitoyl sphingomyelin, and distearoyl sphingomyelin.

The lipid composition of both the initial powdered composition of matter and the resultant liposomes, formed in accordance with the present method, is normally the same. Where the resultant liposomes are intended for in vivo applications (such as drug delivery), then it is normally desirable that the lipid composition have a transition temperature below body temperature. Liposomes composed of phospholipids which have transition temperatures below the characteristic gel-liquid crystalline phase transition temperature of biological membranes, i.e. about 37° C., are considered fluid and those which have transition temperature above 37° C. are considered solid. Another consideration in selecting the composition of lipid or lipids for liposome applications is that alkyl-ether linked lipids (rather than ester linked) are more stable to hydrolysis, and hence alkylether linked lipids for the resultant liposomes may be particularly desirable for therapeutic application.

In addition, other lipid-like substances such as steroids, cholesterol, aliphatic amines or acids such as long chain aliphatic amines or carboxylic acids, long chain sulfates and phosphates, dicetyl phosphate, butylated hydroxytoluene, tocopherol, and isoprenoid compounds may be intermixed with the phospholipid components to confer certain desired and known properties on the initial liposomes and hence the resultant liposomes. Further, synthetic phospholipids containing either altered aliphatic portions, such as hydroxyl groups, branched carbon chains, cycloderivatives, aromatic derivatives, ethers, amides, polyunsaturated derivatives, halogenated derivatives, or altered hydrophillic portions containing carbohydrate, glycol, phosphate, phosphonate, quaternary amine, sulfate, sulfonate, carboxy, amine, sulfhydryl, imidazole groups and combinations of such groups, can be either substituted or intermixed with the phospholipids.

The antifungal polyene macrolides of the present invention include nystatin, amphotericin B, partricin and derivatives thereof such as methyl esters.

These examples are presented to illustrate preferred embodiments and utilities of the present invention and are not meant to limit the present invention unless otherwise stated in the claims appended hereto.

EXAMPLE 1

Preparation and Use of a Pre-Liposomal Nystatin Powder (L-Nys)

A solution of 25 mg nystatin in 25 ml methanol was mixed with a solution of 175 dimyristoylphosphatidylcholine (DMPC) and 75 mg dimyristoylphosphatidylglycerol (DMPG) in 10 ml chloroform. The DMPC:DMPG ration was 7:3 and the nystatin:DMPC+DMPG ration was 1:10. The organic solvents were then evaporated at 40° C. under partial vacuum in a rotary evaporator until a dried lipid film was formed. Thirty ml of 2:1 mixture of tertiary butanol and methylene chloride were added to dissolve the dried lipid film. The organic were then evaporated from the solution at 40° C. and under partial vacuum to form a lipid residue. The lipid residue was dissolved in tertiary butanol and the solution passed through a 0.2 um filter. The nystatin concentration was measured from an aliquot of the filtrate. The filtrate was frozen by immersion of a container in dry ice-acetone. The frozen material was subjected to overnight lyophilization and a fine preliposomal nystatin powder produced.

A 100 mg sample of the fine powder (containing about 10 mg nystatin) was suspended with 10 ml of pyrogen-free saline. When the powder suspension was warmed at 40° C. for 2–5 minutes, liposomes were formed therein. As determined by microscopic examination, the suspended materials were 100% liposomes were formed therein. As determined by microscopic examination, the suspended materials Were 100% liposomes and no crystals were found. The suspension was centrifuged at 20,000 rpm (40,700×g) for one hour and the resultant pellet removed and resuspended in saline. The nystatin remaining in the resuspended pellet was determined to be 70–80 percent of the original amount added, by dissolution in methanol and measurement of optical density at 306 nm. The encapsulation efficiency of the liposomes, as measured after the filtration step, was observed to be >99%. (No detectable free drug was left after formation of liposomes from the powder). The resuspended pellet was a liposome preparation substantially free of soluble lipids or other materials and was suitable for clinical administration.

EXAMPLE 2

Preparation and Use of a Pre-Liposomal Amphotericin B Powder

Amphotericin B in methanol and phospholipids (DMPC:DMPG, 7:3) in chloroform were mixed together in a ratio of 1:10. The organic solvents were then evaporated at 40° C. using a rotary evaporator under vacuum.

Tertiary butanol and methylene chloride in a 1:30–40 ratio were added to solubilize the dried lipid film. The organic solvents were then evaporated.

The residue in the flask was then dissolved in tertiary butanol, warmed to temperatures above 52° C., and filtered through a 0.2 um filter. An aliquot from this filtrate was taken to determine the amphotericin B concentration.

The above mixture was then frozen (using dry ice with acetone) and lyophilized overnight. A fine powder was obtained.

The powder obtained as described above was suspended in pyrogen-free saline. The liposomes did not form until the suspension was warmed in a water bath at about 40° C. for about 2–5 minutes. The suspension then formed 100% liposomes (no crystals), as they appeared under a microscope. The suspension was centrifuged at 20,000 rpm for one hour and the pellet removed and resuspended in saline. An aliquot was taken from this final suspension and the amount of amphotericin B incorporated into liposomes quantitated by dissolving in methanol and measuring O.D. at 405 nm. The encapsulation efficiency of drug from the powder to liposomes was 99–100%.

Changes may be made in the elements and methods described herein or in the steps or the sequence of steps of the method described herein without departing from the concept and scope of the invention as defined in the following claims.

What is claimed is:

1. A process for producing a powder which forms liposomes comprising an antifungal polyene macrolide upon suspension in an aqueous solution, said process comprising the steps of:
   (a) dissolving antifungal polyene macrolide and phospholipids in a quantity of first organic solvent and a quantity of second organic solvent respectively, to form a first solution and a second solution;

(b) mixing the first solution and the second solution to form a mixture;

(c) removing the first organic solvent and the second organic solvent from the mixture to form a residue;

(d) dissolving the residue in a quantity of a third organic solvent to form a third solution, wherein the third organic solvent comprises tertiary butanol and methylene chloride;

(e) extracting the third organic solvent from the third solution to leave a remnant;

(f) forming a fourth solution by dissolving the remnant in a solvent consisting essentially of tertiary butanol;

(g) passing the fourth solution through a filter having orifices with diameters of between about 0.05 um and about 0.5 um to produce a filtrate; and (h) lyophilizing the filtrate to remove the solvent consisting essentially of tertiary butanol.

2. The process of claim 1 wherein the antifungal polyene macrolide is nystatin, amphotericin B, partricin or a derivative thereof.

3. The process of claim 1 wherein the antifungal polyene macrolide is nystatin or amphotericin B.

4. The process of claim 1 wherein the antifungal polyene macrolide is amphotericin B.

5. The process of claim 1 wherein the antifungal polyene macrolide is nystatin.

6. The process of claim 1 wherein the phospholipids are one or more of phosphatidylcholine, phosphatidylserine, phosphatidylglycerol, sphingomyelin and phosphatidic acid.

7. The process of claim 1 wherein the phospholipids comprise DMPC and DMPG.

8. The process of claim 1 wherein the phospholipids consist essentially of DMPC and DMPG in 7:3 ratio.

9. The process of claim 1 wherein the first solvent is methanol.

10. The process of claim 1 wherein the second solvent is chloroform.

11. The process of claim 1 wherein step (b) is defined further as:

mixing the first solution and the second solution to form a first mixture having a ratio of antifungal polyene macrolide to phospholipid between about 1:5 and about 1:50.

12. The process of claim 1 wherein step (b) is defined further as:

mixing the first solution and the second solution to form a first mixture having a ratio of antifungal polyene macrolide to phospholipid of about 1:10.

13. The process of claim 1 wherein step (c) is defined further as:

removing the first solvent and the second solvent from the first mixture by subjecting the first mixture to solvent evaporation under reduced pressure and at a temperature between about 35° C. and about 45° C.

14. The process of claim 1 wherein, prior to the passing step, the fourth solution is clarified by warming to between about 50° C. and about 70° C.

15. The process of claim 1 wherein the third organic solvent comprises tertiary butanol and methylene chloride in a ratio between about 2:1 and about 1:40.

16. The process of claim 1 defined further wherein the filter has orifices of about 0.2 um.

17. The process of claim 1 wherein the antifungal polyene macrolide and phospholipids are in a ratio of between about 1:5 and about 1:20.

18. The process of claim 1 wherein the antifungal polyene macrolide and phospholipids are in a ratio of about 1 to 10.

* * * * *

UNITED STATES PATENT AND TRADEMARK OFFICE
CERTIFICATE OF CORRECTION

PATENT NO. : 4,950,432

DATED : August 21, 1990

INVENTOR(S) : Reeta Mehta, et al

It is certified that error appears in the above-identified patent and that said Letters Patent is hereby corrected as shown below:

In column 1, line 37, "lyaphoreticular" should be --lymphoreticular--.

In column 8, line 6, "Were" should be --were--.

Signed and Sealed this

Fourteenth Day of January, 1992

Attest:

HARRY F. MANBECK, JR.

Attesting Officer      Commissioner of Patents and Trademarks